United States Patent [19]
Warrin

[11] 4,276,024
[45] Jun. 30, 1981

[54] CONTROL SYSTEMS FOR DENTAL HANDPIECES

[75] Inventor: George E. Warrin, North Merrick, N.Y.

[73] Assignee: Cavitron Corporation, New York, N.Y.

[21] Appl. No.: 32,792

[22] Filed: Apr. 23, 1979

Related U.S. Application Data

[62] Division of Ser. No. 780,638, Mar. 28, 1977.

[51] Int. Cl.³ .................................................. A61C 1/10
[52] U.S. Cl. ....................................... 433/99; 60/407; 415/503
[58] Field of Search ............... 60/407; 415/51, 503; 433/99; 173/169, 170

[56] References Cited

U.S. PATENT DOCUMENTS

| | | |
|---|---|---|
| 3,125,809 | 3/1964 | White . |
| 3,250,005 | 5/1966 | White . |
| 3,346,958 | 10/1967 | Sinatra .................................. 433/99 |
| 3,430,710 | 3/1969 | Coss ..................................... 173/169 |
| 3,568,318 | 3/1971 | Martin . |
| 3,676,931 | 7/1972 | Pletschmann . |
| 3,842,504 | 10/1974 | Ricks ..................................... 251/57 |
| 3,955,283 | 5/1976 | Mehallick ............................. 433/99 |
| 3,959,883 | 6/1976 | Walls et al. ........................... 91/459 |
| 4,051,337 | 9/1977 | Warrin ................................ 200/61.85 |
| 4,205,236 | 5/1980 | Goof ...................................... 433/99 |

Primary Examiner—Louis J. Casaregola
Attorney, Agent, or Firm—Robert M. Skolnik; William R. Evans

[57] ABSTRACT

A system controls the flow of a drive fluid for driving a tool on a handpiece. The system comprises a drive fluid line communicating with the handpiece and a drive fluid control motor for controlling the flow of the drive fluid in the line. Control means is operatively associated with the fluid drive motor control, and responsive actuation means on the handpiece which is manually engaged by the finger of the user. Upon actuation, the control means controls the drive fluid control to provide initially a flow of the drive fluid such that the handpiece is powered at an initial level, the fluid motor then being continuously responsive for a time interval substantially coinciding with the operation of the actuation means by the finger of the user for altering the level of drive fluid flow to vary the power available in the handpiece. The level of flow when the finger releases the actuation means is then maintained until the actuation means is again actuated whereupon drive fluid flow is stopped.

11 Claims, 17 Drawing Figures

OFF-BEFORE ACTUATION

FINGER RELEASED-
ON

TOUCH AND RELEASE-
OFF

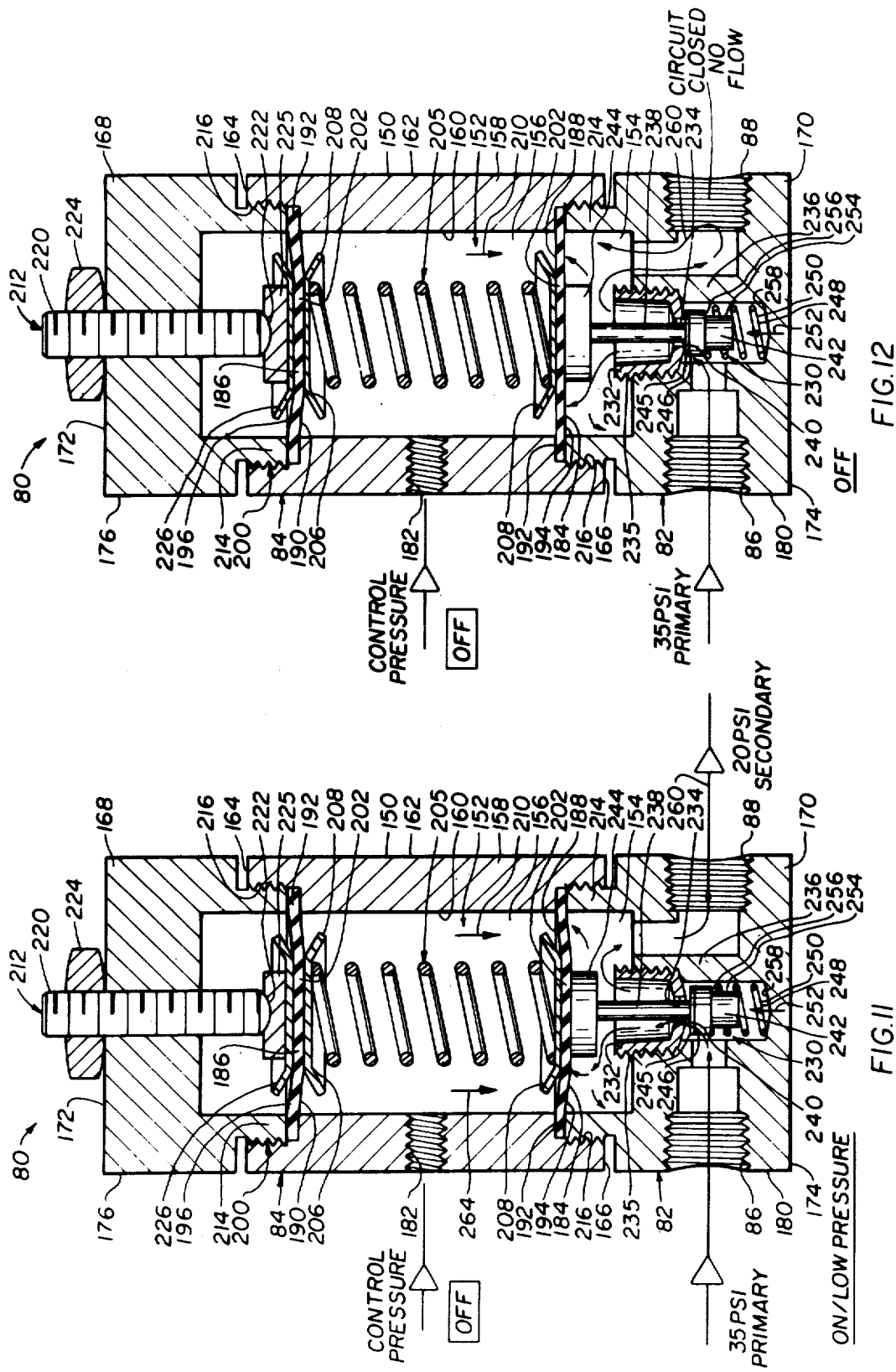

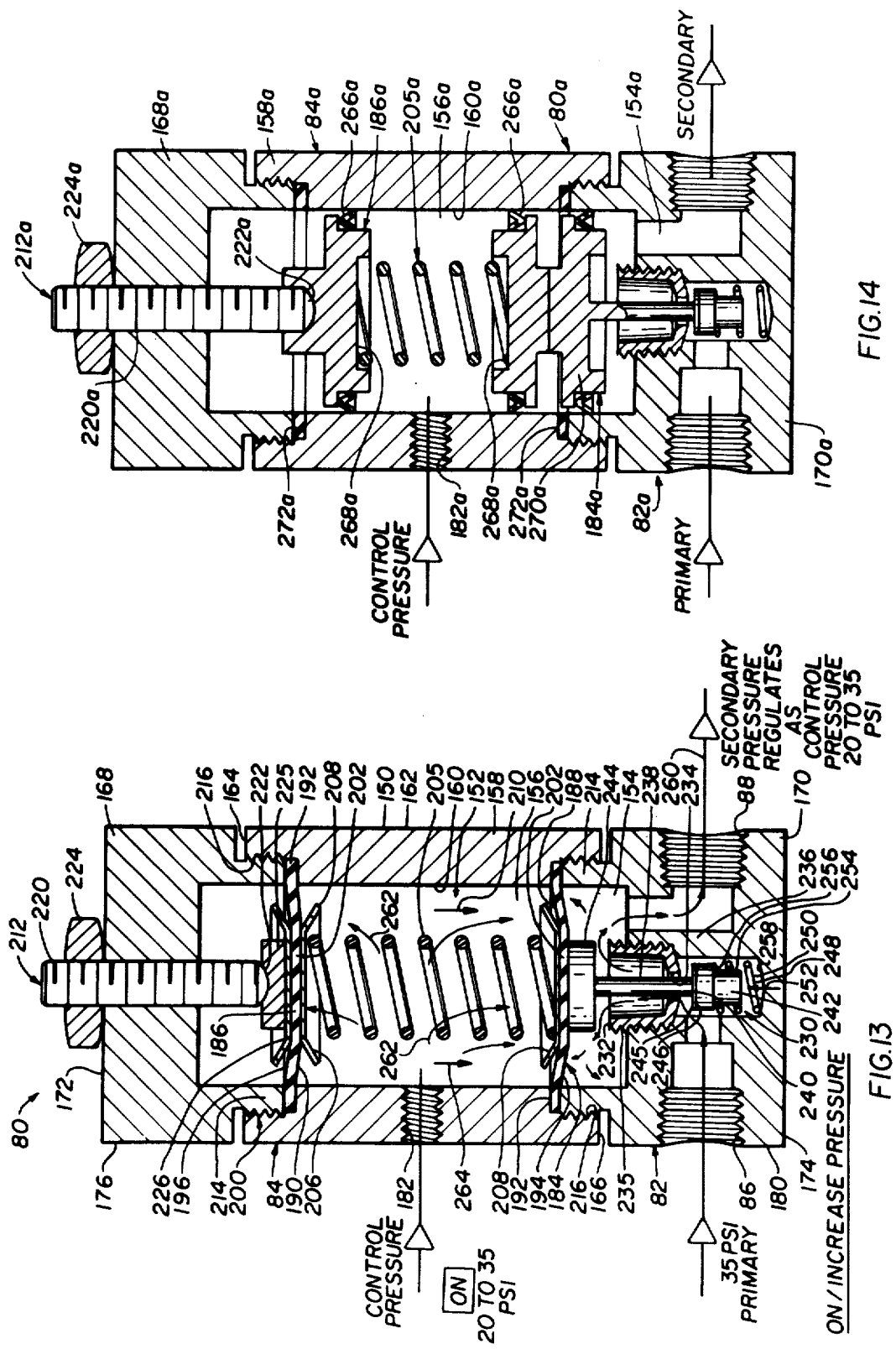

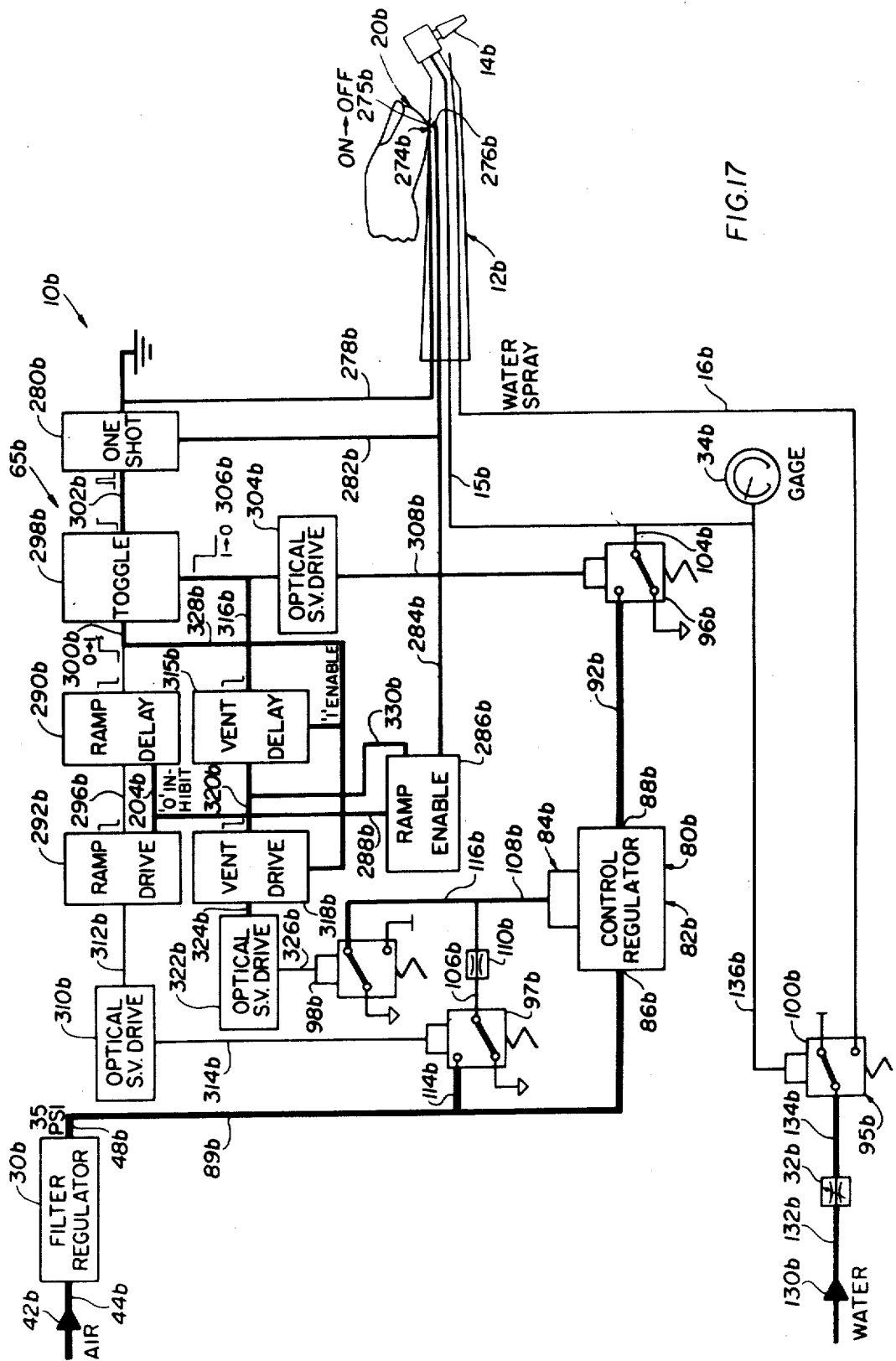

CONTROL SYSTEMS FOR DENTAL HANDPIECES

This is a division of application Ser. No. 780,638, filed Mar. 23, 1977.

BACKGROUND OF THE INVENTION

The present invention pertains to control systems for fluid driven motors.

More particularly, it pertains to dental handpieces that are fluid driven and the manner of controlling the speed thereof. Although the present invention will be particularly illustrated and discussed with respect to such fluid driven dental handpieces, it is appreciated that the invention is applicable to other fluid powered devices and is therefore not limited to dental applications.

DESCRIPTION OF THE PRIOR ART

The use of fluid driven dental handpieces, and particularly air driven handpieces, is well known and widely accepted by the dental profession. It has also been appreciated in the prior art that using the dentist's hand that is holding the handpiece for also controlling the speed of the handpiece would provide an advantage to the dentist. By providing the dentist with finger-tip speed control, his foot need not be used for speed control as is now common practice.

An attempt to provide finger-tip control to a fluid driven dental handpiece is disclosed in U.S. Pat. 3,568,318 to J. C. Martin. In practice, however, a dental handpiece is started at a minimal level or speed and the speed then increased to a desired level up to and including a maximum level or speed. Speeds set and retained upon removing a foot from the control are presently available to the dentist when utilizing a foot-controlled speed-changing device. It is therefore competitively required that the finger-tip system also readily permit selecting and retaining a speed upon removal of the finger from the controls. The invention Martin discloses fails to provide this most necessary control. In contrast to the disclosure in the patent to J. C. Martin, the present invention provides the dentist with this ability.

Accordingly, the present invention can eliminate foot controllers from the dental office along with all the inherent drawbacks associated therewith, such as limiting the dentist's range of movement. Although the finger-tip controls described herein as illustrated on a dental handpiece, it is again to be appreciated and understood that those controls may be mounted on other instruments, equipment, etc., that may be readily engaged by the user of the instrument or some other person in close proximity thereto.

OBJECTS OF THE INVENTION

An object of the present invention is to provide a system for use with a dental handpiece or the like that is adapted to be pwered by a fluid such as air, the sytem having finger-tip controls for controlling the speed thereof.

Another object of the present invention is to provide apparatus for controlling the speed of air-driven tools utilized on a handpiece with finger-tip controls for controlling and selectively setting the speed of the tool on the handpiece.

Another object of the present invention is to provide apparatus having finger-tip controls on a handpiece with interrelated means adapted to permit initial almost instantaneous starting of the handpiece and selectively increasing the speed of the tool in the handpiece by finger-tip control, and thereafter removing the finger from the controls while the speed of rotation of the tool is retained at the final speed before removal of the finger from the controls.

Another object of the present invention is to provide a handpiece in which either fluidic or electical finger-tip actuated controls may be utilized in a manner to vary the flow of fluid to the handpiece, and thereafter deenergizing the system by finger-tip contact with the controls.

Other objects and advantages of the present invention will become apparent as the disclosure proceeds.

SUMMARY OF THE INVENTION

The outstanding and unexpected results obtained by this invention arise from a series of features and elements and working together in interrelated combination. The preferred is adapted to be used with a dental handpiece or the like having a fluid drive line communicating therewith. In addition, a cooling fluid line also may be provided to supply a cooling fluid to the handpiece.

The system of the present invention includes a drive fluid control motor that may be comprised of a pressure transducer and a regulator operating with each other to regulate and maintain selective rates of drive fluid flow under pressure to the dental handpiece through a drive fluid line. The pressure transducer means has an inlet and an outlet for the flow of the drive fluid therethrough, with the inlet communicating with a source of fluid at a certain pressure, and the outlet communicating with the drive fluid line for powering the handpiece. The regulating means is thus utilized for varying the handpiece.

The system of the present invention further provides a control operatively associated with the drive fluid control motor and actuation means that may be mounted on the handpiece for manual engagement by the user thereof.

The actuation means, in one embodiment of the present invention, is fluid operated in conjunction with a fluidic control. In this embodiment the actuation means comprises a vent orifice normally vented to atmosphere and communicating with control via a fluid line. the actuation means is operated by substantially closing the orifice such that the control fluid is deflected to power the control.

The control makes the regulating means responsive to the time interval that the vent orifice is substantially closed for altering the flow of the drive fluid through the pressure transducer means and maintaining the altered levle of flow subsequent to the vent orifice being rendered open.

The control comprises fluidic switching means in accordance with the embodiment being discussed and a plurality of valves operative between open and closed positions to direct the flow of the drive fluid. The control fluid is utilized to power the respective values between the open and closed positions. In this manner the switching means is activated by the flow of control fluid therein when the vent orifice is rendered substantially closed.

After the dentist sets the handpiece to a particular speed, level he thus removes his finger from overlapping relationship with the vent orifice and the system is set at the then flow rate to drive the tool on the handpiece. At such later time as the dentist wishes to turn the handpiece off or reset the handpiece to a different speed, the finger is momentarily brought back into overlapping relationship with the vent orifice. This again deflects the flow of air from the vent orifice to the switching means. The switching means is then cycled to close one of the valves which prevents further supply of drive fluid to the handpiece and at the same time open another valve to vent the regulator to the atmosphere.

When this condition is met, the system can be recycled to bring the handpiece to another desired speed. The actual cycling of the handpiece to an off condition and thereafter to another on position at a different level of drive fluid to the handpiece, may take place within seconds. In this manner the dentist does not lose continuity in the dental procedure. The dentist can therefore readily change the speed of the drill by finger-tip control even while the tool remains within the mouth of the patient and the dentist continues to perform his procedure.

In accordance with another embodiment of the present invention, the actuation and control are electrical. The actuation means then comprise a pair of contacts which when brought into engagement with each other energize the control. The electrical control still functions in a manner to regulate the drive fluid motor means control to obtain and maintain rotation of the tool in the handpiece at a desired speed.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

FIG. 11 is a cross-section along lines 11—11 of FIG. 10;

FIGS. 12 and 13 are views similar to that of FIG. 11 showing the fluid motor in other operating positions;

FIG. 14 illustrates another embodiment of a fluid motor that may be utilized within the system illustrated in FIGS. 3-7;

FIG. 17 is a view similar to FIG. 15 illustrating the system of FIG. 15 in its final operating position.

DETAILED DESCRIPTION OF PREFERRED EMBODIMENTS IN THE DRAWINGS

Figure 1:
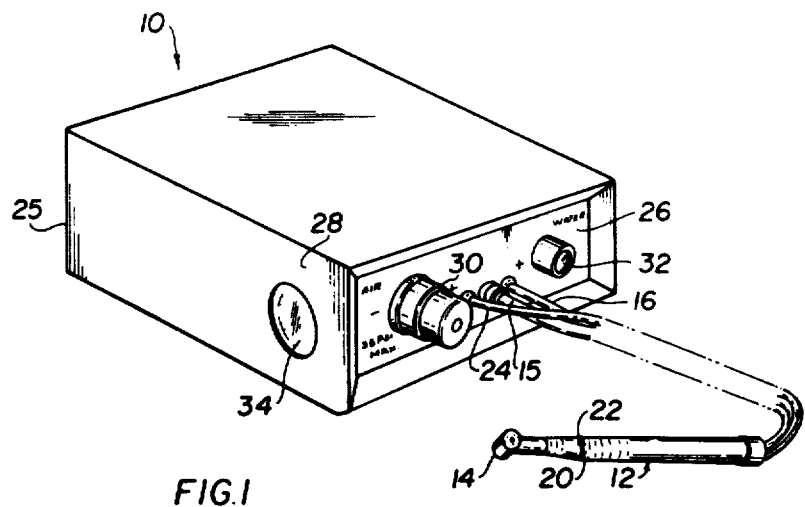
FIG. 1 is a perspective view of a dental handpiece or the like operatively connected to a cabinet for containing the various controls of the present invention.

Referring to the drawings, and initially to FIG. 1 thereof, there is illustrated a system or assembly 10 for controlling the flow of a drive fluid, which may be air, to a handpiece 12 having a working tool or tip 14 operatively extending outwardly therefrom. The handpiece 12 is well known in the dental art and includes a tool rotation motor (air turbine) and a tool drive fluid line 15 communicating with the handpiece 12. When the handpiece 12 is utilized for dental applications, there is also provided a coolant line or conduit 16 for providing a flow of coolant fluid from the handpiece. In accordance with the embodiment of the invention illustrated in FIGS. 1 through 7, still another source of fluid, such as air, is utilized to control and actuate the system 10 to obtain various speeds of rotation of tool 14. To accomplish this, actuation means 20 is provided on the handpiece 12. The actuation means 20 is here in the form of a vent orifice 22 normally vented to atmosphere and communicating with a control fluid line 24.

The system 10 includes a housing or cabinet 25 which contains various fluidic components hereinafter discussed with respect to FIGS. 3 through 7. The cabinet 25 also includes a front panel 26 and a side panel 28. Mounted on the front panel 26 are the connections for the drive fluid line 15, coolant line 16 (usually for water) and control fluid line 24. It is appreciated that both the drive fluid and control fluid may be provided from the same or alternate sources of supply when both are the same fluid, e.g. air.

The equipment has a pressure regulator 30 that is illustrated on the front panel 26. The other adjustment that is provided there is a coolant regulator 32 which is adjusted to select the amount of coolant fluid that flows to the handpiece 12 and exits at or near the tool 14. In addition, a gauge 34 is mounted to be viewed through side panel 28 and coupled within the system 10 to read the drive fluid pressure being provided through drive fluid line 15 to the handpiece 12. Conventional means for powering the system 10 may be provided in a manner well known from a source of compressed fluid under pressure, as well as a supply of coolant, which may be water.

Figure 2:
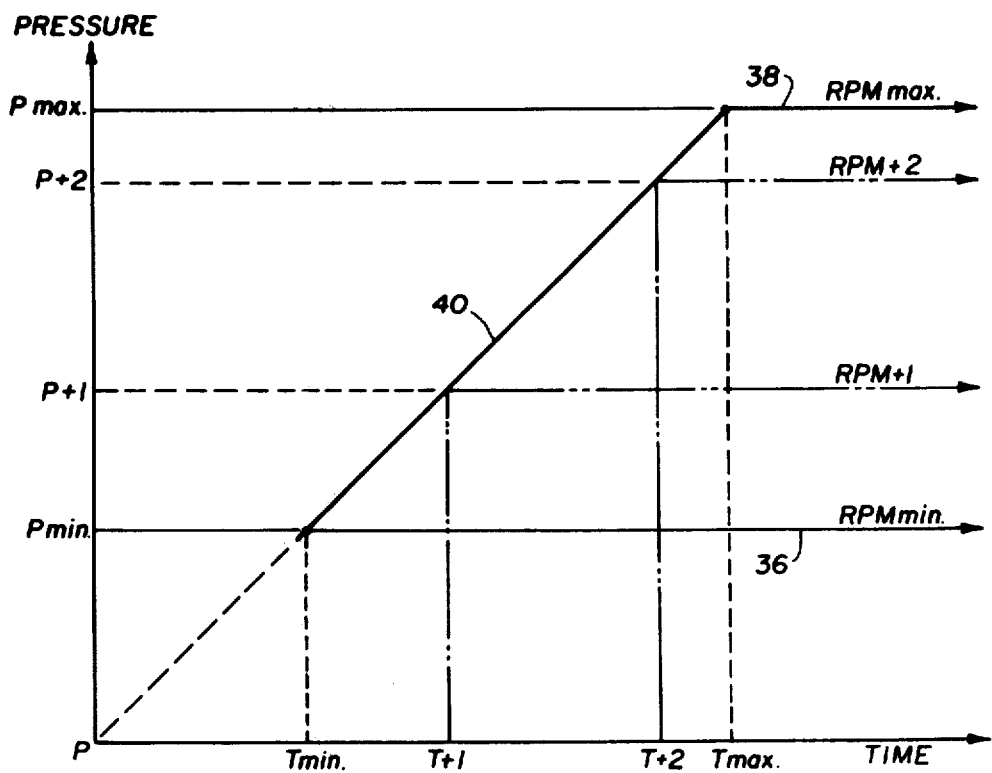
FIG. 2 is a graph to illustrate the ability of the present invention to selectively control the speed of rotation of a tool mounted on the handpiece.

FIG. 2 has been provided to help illustrate the operation of the system 10 as dictated by the needs of the user, and the ability of the system to respond on an almost instantaneous basis to control the speed of rotation of the tool 14. The graph on FIG. 2 is plotted to indicate drive fluid pressure as related to control time. In contrast to the prior art hereinabove discussed, the user has the ability by mere manipulation of his or her finger over the vent orifice 22 to actuate the system 10, and thereafter dependent upon the period of time that the flow of control fluid is prevented from exiting from the vent orifice 22, the speed of rotation of the tool 14 will be increased. The vent orifice 22 therefore is positioned on the handpiece 12 such that it is readily momentarily sealed or closed by the forefinger of the user dentist.

The handpiece 12 is selected such that with a flow of drive fluid through drive line 15 at P min., tool 14 rotates at RPM min. revolutions per minute indicated at 36. In similar fashion a maximum speed of rotation of tool 14 (RPM max. at 38) is obtained when the fluid pressure in line 15 reaches P max.

The time span T min. to reach the speed RPM min. is indicated by the dashed part of graph line 40 and may be approximately 0.2 seconds. The time T max. to reach maximum tool speed RPM max. may be reached in approximately 2 seconds from the time that control fluid is prevented from exiting through orifice vent 22. The above parameters as indicated by the solid part of line 40 may vary depending upon design, use, etc.

The present invention, merely by momentarily closing off vent orifice 22, thus can selectively obtain often desired speeds of rotation intermediate RPM min. and RPM max. Further, upon removal of the person's finger from vent orifice 22, the system will remain stable at the selected speed.

This feature is most important since the dentist can select a desired speed of rotation, as dependent upon his particular needs. For example, the dentist may retain his finger over the vent orifice 22 for a period of time indicated on the chart in FIG. 2 as T+1. This in turn results in a drive pressure of P+1 and thus a tool speed of RPM+1 greater than RPM min. If a greater speed is then required, the user would merely restrict or block the flow of control fluid for a period of time T+2 (after having intermediately blocked the flow to reset the control as described in the next paragraph). As illustrated by line 40 on the graph T+2 coincides with a pressure of P+2 and a speed of RPM+2. It is appreciated that the graph in FIG. 2 is provided merely to aid in the understanding and appreciation of the invention, and that the times required to reach appropriate speeds may vary from system to system.

Once the tool has reached the desired speed, the dentist is free to return his foreginger to another position on the handpiece until such time as the dentist desires to turn the equipment completely off, or select another speed of rotation for the tool 14. The novel system 10 of the present invention permits the dentist to merely reestablish the position of his finger over vent orifice 22 for a momentary period of time, to vent at least the drive of system 10 and return it to a pressure level of P which is generally at a zero pressure. To thereafter initiate powering of the tool 14, the finger is again placed over the vent orifice 22. A momentary placement of the finger will set the system 10 at RPM min. at P min. and increasing the speed up to and including RPM max. at P max. is then directly proportional to the succeeding continuous time that the vent orifice 22 is blocked.

Although the vent orifice 22 has been discussed for finger, it is appreciated that any closure element may be used.

Figure 3:
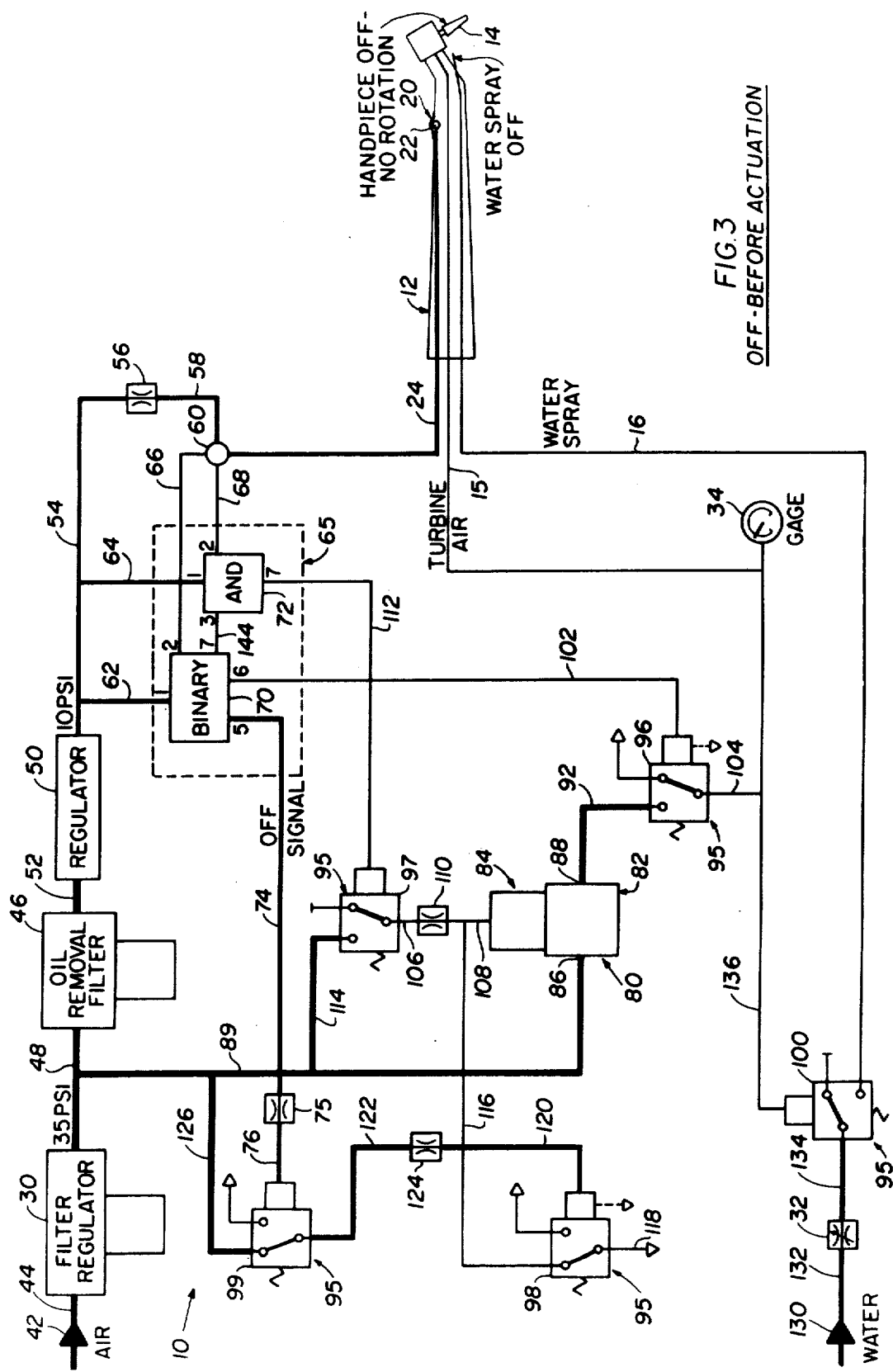
FIGS. 3-7 are flow diagrams, partially in schematic form, illustrating the system during sequential operation thereof to obtain the desired powering of the handpiece.

FIGS. 3 through 7 illustrate the various components of the system 10 working in interrelated combination with each other through the various sequences of operation. FIG. 3 initially illustrates the system 10 in an "OFF" condition before actuation. The system 10 is supplied with a source of drive and control fluid indicated by flow arrow 42 which is coupled by conduit or line 44 to the regulator 30 which may also include a filter. The initial pressure of the fluid supply is illustrated at 35 PSI. An oil removal filter 46 is connected by conduit 48 to the pressure regulator 30. A control pressure regulator 50 is connected to the oil removal filter 46 by conduit 52. The control pressure regulator 50 can be adjusted to step down the control fluid pressure, e.g. from 35 PSI to 10 PSI. The pressure control fluid reduced is then free to flow through conduit 54 and a restrictor 56 to a junction member or means 60. One branch extending from the junction member 60 is the control fluid line 24 which extends to and within the handpiece and terminates at the venting orifice 22 illustrated in FIG. 3.

Branch conduit tubes 62 and 64 extend from conduit 54 and are coupled to switching means 65. The switching means 65 is operatively connected to the actuation means 20 (vent 22) by conduits 66 and 68 and junction member 60 in later described conditions. In this embodiment of the invention the switching means 65 comprises fluidic control means 70 and 72 operating in conjunction with each other and the other portions of the system 10 in the manner hereinafter described.

At the time illustrated in FIG. 3, there are two pressures in certain conduits within the system 10. The lower pressure being at 10 PSI, for example, is contained within conduits or fluid lines 24, 54, 58, 62, 64, 74 and 76. Conduit 74 extends from control means 70 into a restrictor 75 with conduit 76 extending therefrom. The restrictors 56 and 75 are provided to further assure proper pressure and flow through the system 10.

System 10 further includes fluid motor means 80, as further discussed and illustrated with respect to FIGS. 8 through 14. The fluid motor means 80 is comprised of pressure transducer or fluid valve means 82 that operates in conjunction with fluid regulating means 84. The pressure transducer means 82 includes an inlet 86 and an outlet 88. Conduit 89 extends between conduit 48 and inlet 86 to supply drive fluid to motor 80 at the pressure selected by pressure regulator 30.

An outlet conduit 92 from outlet 88 communicates with the drive fluid line 15 for powering the handpiece. The fluid motor means 80 is adjustable between selected levels for regulating the flow of the drive fluid to the handpiece 12. The outward flow through conduit 92 is related to the pressure indicated on the chart in FIG. 2, which ranges between P min. and P max. It is the pressure in conduit 92 that has to be selectively controlled to vary the speed of rotation of the tool 14.

Operating in conjunction with the fluid motor means 80, switching valve means 65, and the control fluid line 24 and drive fluid line 15 is control valve means 95. The control valve means 95 may include a plurality of individual valves 96, 97, 98, 99 and 100 that are fluidic operated so as to permit the flow, or prevent the flow, of the control and drive fluid through various portions of the system 10. First valve means 96 is operatively associated with pressure transducer means 82 by conduit 92, drive fluid line 15, and switching valve means 65. Conduit 102 connects fluidic control means 70 to first valve means 96. First valve means 96 is in turn connected by conduit 104 to drive fluid line 15. The drive fluid line 15 has pressure gauge 34 operatively associated therewith to indicate the pressure entering the handpiece 12 through drive fluid line 15.

Figure 4:
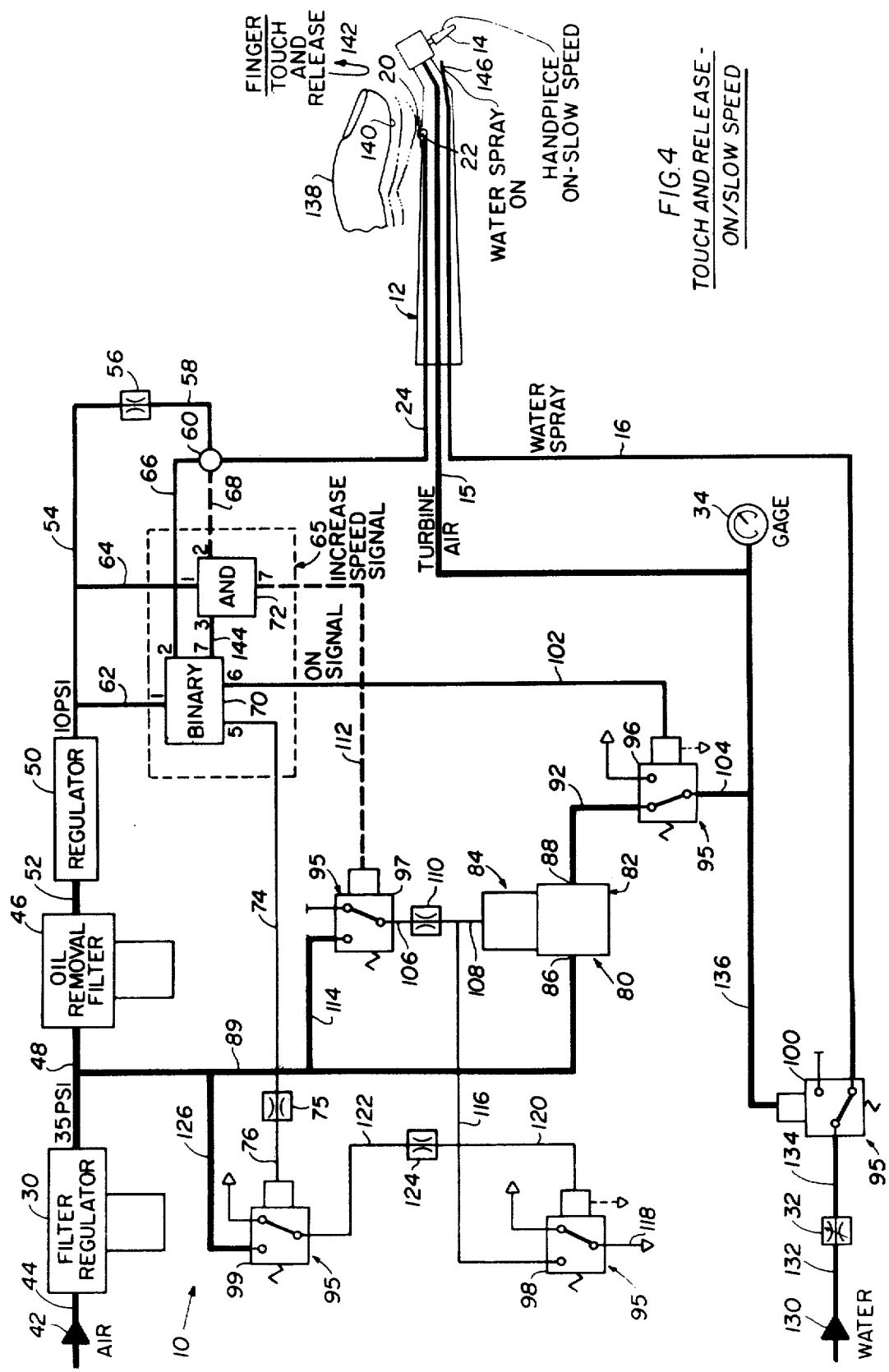
Figure 5:
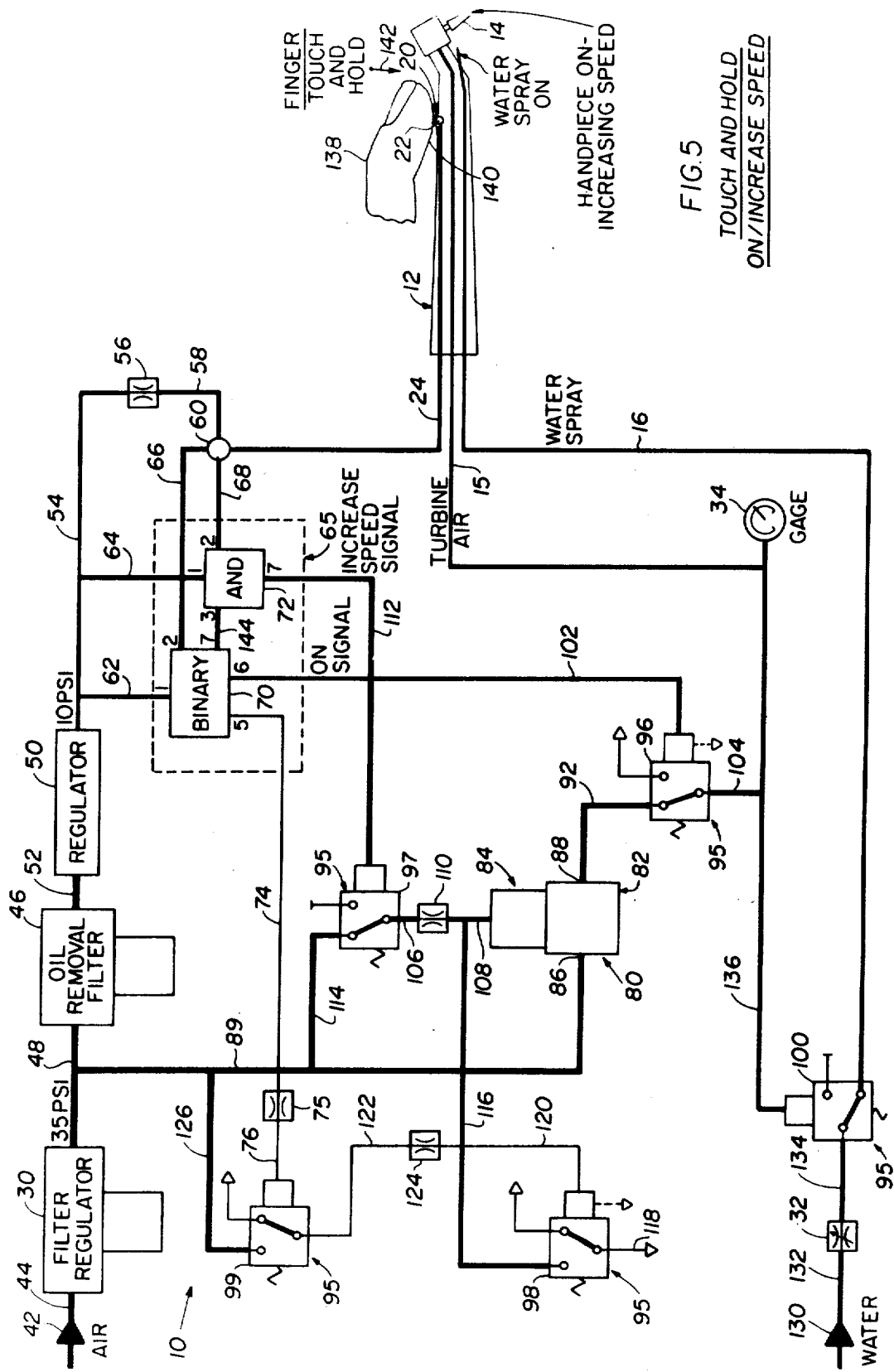
Figure 6:
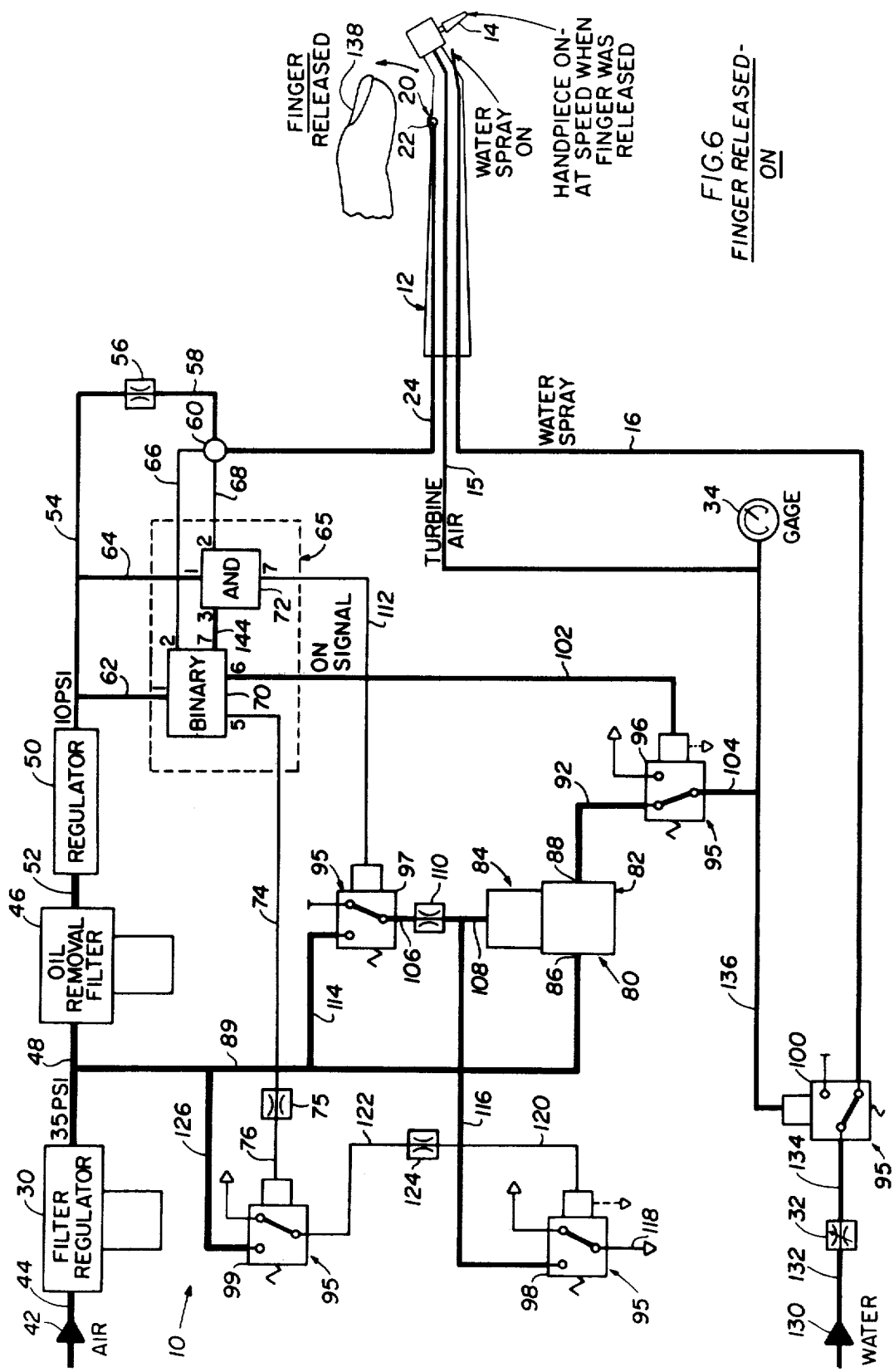

The first valve means 96 is operative between a closed position, as illustrated in FIG. 3, and an open position, as illustrated in FIGS. 4, 5, and 6, for permitting the flow of the drive fluid from the pressure transducer means 82 to the drive fluid line 15. First valve means 96 is fluidic actuated by the switching or power means 65 through conduit 102.

Second valve means 97 is operatively associated with the regulating means 84 through conduits 106 and 108 having a restrictor 110 therebetween. The second valve means 97 is controlled by conduit 112, which is connected to control means 72 for a flow of control fluid therethrough. Conduit 114 extends between conduit 89 and the input end of second valve means 97. Second valve means 97 is operative between open and closed positions. The closed position is illustrated in FIGS. 3, 4, 6 and 7. The open position is illustrated in FIG. 5. The open position, as illustrated in FIG. 5, permits a flow of pressurized drive fluid to enter the regulating means 84 so as to perform a function hereinafter discussed with particular reference to FIGS. 11, 12 and 13.

Third valve means 98 is operatively associated with the second valve means 97 and the regulating means 84 via conduit 116. Third valve means 98 is utilized within the system 10 for venting the regulating means 84 as required. The third valve means 98 is illustrated in its open position, which is vented to the atmosphere through outlet part or conduit 118, in FIGS. 3 and 7. FIGS. 4, 5 and 6 illustrate third valve means 98 in its closed position.

Fourth valve means 99 is operatively associated with third valve means 98 through conduits 120 and 12 which may have a restrictor 124 therebetween. The flow of drive fluid through conduits 120 and 122 is used to activate the third valve means 98. Fourth valve means 99 is activated between open and closed positions by control fluid entering through conduits 74, 75, 76. Conduit 126 is connected to conduit 89 and in turn conduit 48 such that pressurized fluid from the initial source indicated at 42 is always available at one of the valve ports on fourth valve means 99.

The fourth valve means 99 operates between open and closed positions. The open positon illustrated in FIGS. 3 and 7 permits pressurized fluid to flow through fourth valve means 99 to the third valve means 98. The fourth valve means 99 is illustrated in its closed position in FIGS. 4, 5 and 6.

As illustrated in FIG. 3 drive fluid pressure is available from the regulator means 30 in conduits, 48, 52, 89, 114, 120, 122, and 126. This pressure is also available in conduit 92 thereby to be almost instantaneously available to the handpiece 12 through drive fluid line 15 as soon as first valve means 96 is activated from the closed position in FIG. 3 to the open position in FIG. 4.

The fifth valve means or coolant valve means 100 is operatively associated with a coolant fluid supply indicated by numeral 130, which may be water, and is available under pressure to flow through coolant regulator 32 via conduit 132. Conduit 134 connects the coolant regulator 32 to the coolant valve means 100. Coolant valve means 100 is operatively associated with first valve means 96 through conduit 136 to provide a supply of drive fluid open the coolant valve means 100 when in the open position illustrated in FIGS. 4, 5, and 6. Coolant, fluid then flows through the open coolant valve means 100 and coolant fluid conduit 16 to exit from the handpiece proximate to the tool 14.

The power or switching valve means 65 is adapted to function in a preselected sequential manner. The components forming the switching valve means, identified as control means 70 and 72, are of a type and construction well known in the art such as types No. 4BB-205-000 and 4AN-203-000, respectively, manufactured by C. A. Norgren Co., 5400 S. Delaware Street, Littleton, Colorado 80120. The part nomenclature of the C. A. Norgren catalog has been provided in the drawings to aid in the discussion and description of the invention.

Control means 70 acts as a binary counter containing an integrated circuit to provide a count function between the respective parts identified by numerals 1, 2, 5, 6, and 7. The control means 72 may be visualized as a pair of normally closed valves connected in series to each other. The numerals 1, 2, 3 and 7 identify parts associated with the device 72 which shifts the flow of fluid and resequences itself if a control signal is removed.

SYSTEM OPERATION

FIGS. 3 through 7 illustrate the various operating conditions of the system 10 and the manner in which the tool 14 is rotated almost instantaneously FIG. 3 shows the system 10 in a ready condition for activation by the user from the handpiece 12. For activation the user initially would place the handpiece 12 in his or her hand and bring the underside 14 of an individual finger 138 into momentary overlap with the venting means defined by the orifice 22 as illustrated by arrow 142 in FIG. 4.

This momentary blockage of vent orifice 22 is sufficient to provide the necessary control signal to control means 70 and 72. FIG. 4 illustrates that the control fluid is now present in conduits 66 and 68, as well as conduit 144 connecting control means 70 and 72 to each other. In addition, conduit 102 from control means 70 is similarly pressurized with control fluid, but conduit 74 is cut off. It will be observed that the conduits throughout FIGS. 3 through 7 are illustrated in either a pressurized condition or an unpressurized condition with the pressurized condition being illustrated by a darkened or thickened line and the unpressurized conduits by a thinner line.

Activation of first valve means 96 from its closed position, as illustrated in FIG. 3, to its open position, as illustrated in FIG. 4, permits the flow of drive fluid from conduit 92 to now flow into conduit 104 and in turn into fluid drive line 15. This flow at the minimal pressure level of the control regulating means 82 is sufficient to power handpiece 12 to obtain a speed of rotation as illustrated in FIG. 2 of RPM min. The regulating means 82 is designed to be activated at P min. so as to assure a fixed minimum speed of rotation of tool 14.

The flow of drive fluid through conduit 104 also branches into conduit 136 to activate coolant valve means 100 from the closed position in FIG. 3 to the open position illustrated in FIG. 4. With the coolant valve means 100 open, the coolant fluid from source 130 is now free to flow through coolant fluid supply line 16 which results in a water spray 146 adjacent the tip 14. The opening of coolant valve means 100 occurs almost concurrently with the opening of first valve means 96 such that the coolant fluid is immediately available at the operative site.

Accordingly, FIG. 4 illustrates the operation of the system 10 such that the minimal preselected speed of the handpiece 12 is readily obtained by a mere momentary closing of the orifice 22. In contrast to the minimal speed, the dentist often requires speeds of rotation of the tool 14 above RPM min. P min. and up to and including RPM max.-P max., as illustrated in FIG. 2. Obtaining speed above RPM min.-P min. requires a flow pressure in conduit 104 above the predeterminedly minimum flow rate through regulating means 82. For example, the drive fluid may be at a pressure of 35 PSI at inlet 86 and at a pressure of 20 PSI at outlet 88 when a minimal flow occurs through regulating means 82. To increase the speed of rotation of tool 14, the pressure in conduit 104 and fluid drive line 15 is increased above P min. This increase may occur up to P max., which may be at approximately 35 PSI. It is appreciated that these pressure ranges are provided for illustrative purposes only.

The dentist, knowing that the desired speed of rotation of tool 14 is to exceed RPM min.-P min., would continue to retain finger 138 in position, as illustrated in FIG. 5. Holding the vent orifice 22 closed with the lower surface 140 of finger 138, actuates control means 72 such that the flow of control fluid through conduit 68 opens the control means 72 to permit a flow into conduit 112, as illustrated by dash lines in FIG. 4 superimposed on the conduit line. This activation results in the opening of second valve means 97 to an open position, as illustrated in FIG. 5.

By opening of the second valve means 97, as illustrated in FIG. 5, conduits 106, 108 and 116 now become pressurized with drive fluid to the pressure controlled by the drive fluid control means 30. The availability of pressure within conduit 108 acts to alter the regulating means 84 to vary the flow-through characteristics of the pressure transducer means 82 to increase same so as to permit an increase in the speed of rotation from RPM min.-P min., up to and including RPM max.-P max.

The regulating means 84 is automatically responsive to the time interval that the vent orifice 22 is rendered substantially closed. During this time interval the flow rate of the drive fluid through the pressure transducer means 82 is altered relative to a given initial or normal level. The user would therefore maintain finger 138 in the position illustrated in FIG. 5 until a desired increased speed of tool 14 is obtained. For example, the speed may be RPM+2, and the pressure in fluid drive line 15 P+2. The time for this to occur is T+2.

An important feature of system 10 is that at the moment finger 138 is retracted from the position illustrated in FIG. 5 to that illustrated in FIG. 6, the fluid motor means 80 remains stable. This permits the dentist to reposition his finger 138 at some other point on the handpiece 12. Until such time as the finger 138 is once again brought into overlapping engagement with vent orifice 22, the flow through the pressure transducer means 82 will remain constant and the speed of the tool 14 is maintained.

At the moment that the finger 138 is retracted, as illustrated in FIG. 6, certain changes occur within the system by activation of the switching means 65 to another condition. When the finger is released, venting orifice 22 will vent the control fluid in control fluid line 24 to the atmosphere. Conduits 66, 68, and 112 no longer have fluid flowing therethrough. This provides a release of second valve means 97 such that it is brought to its closed position. In the closed position of second valve means 97, pressure is contained within conduits 106, 108, and 116. This stabilizes the pressure chamber contained in the regulating means 84.

It will be noted with respect to FIG. 3 that the fourth valve means 99 is in its open position so that conduits 122 and 120 are also pressurized. In contrast, as illustrated in FIG. 4, when only the minimal speed at the low pressure is obtained, fourth valve means 99 returns to its closed position since there is no longer a flow of fluid through conduits 74 and 76. This in turn eliminates the flow of fluid through conduits 120 and 122 thereby permitting third valve means 98 to return to a closed position, as illustrated in FIG. 4. In the interval of time that finger 138 is in operative relationship to the handpiece 12, as illustrated in FIG. 5, fluid pressure is available in conduit 116.

Figure 7:
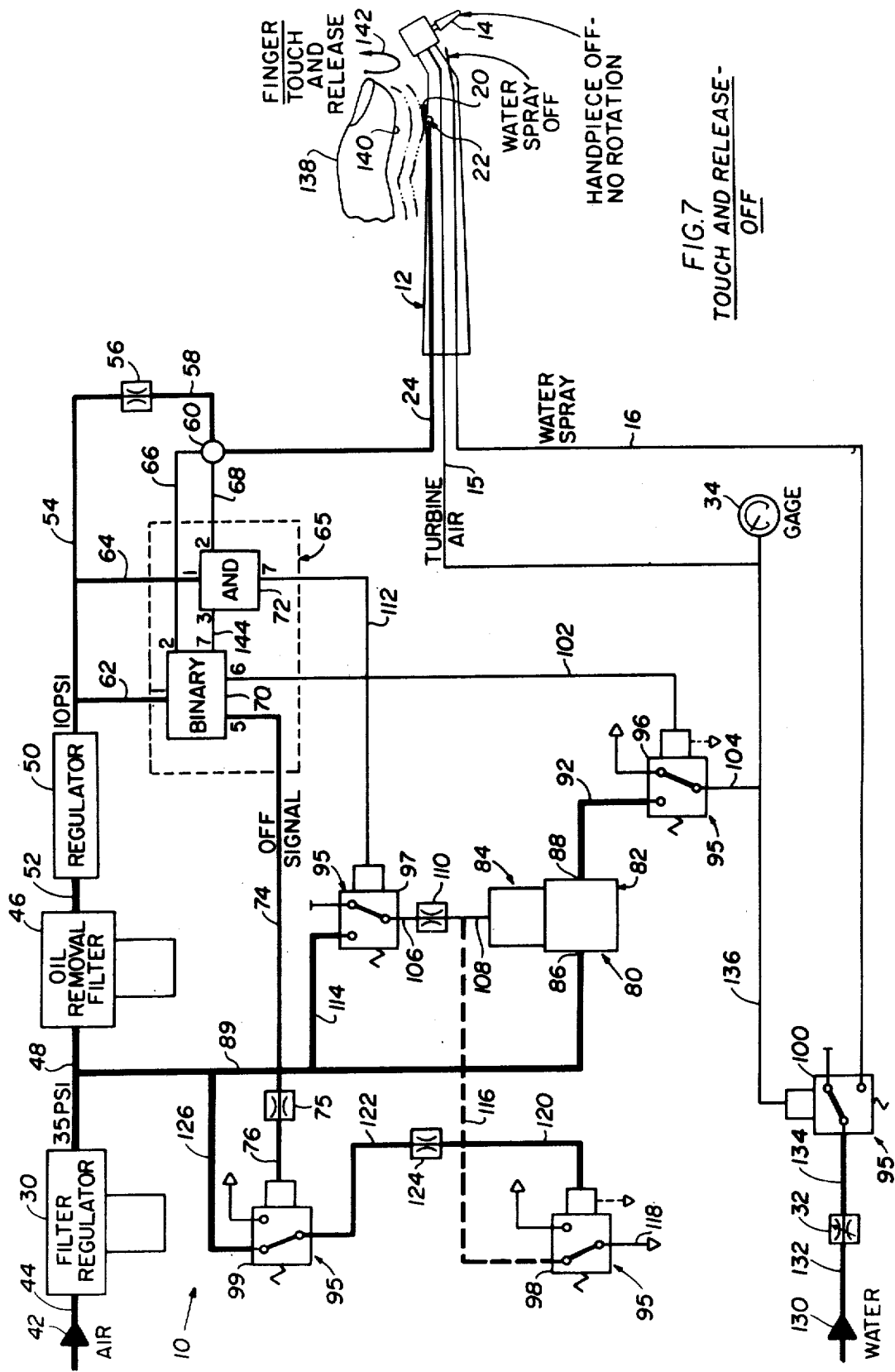
Figure 10:
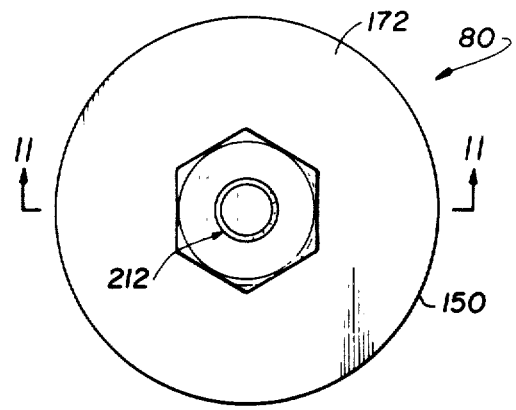
FIG. 10 is a top plan view of the fluid motor illustrated in FIG. 8.
Figure 9:
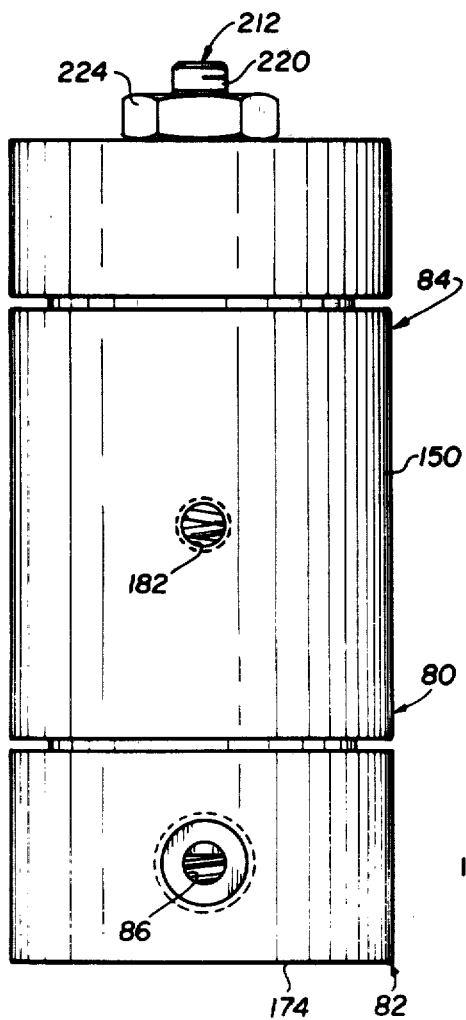
FIG. 9 is a side plan view of the fluid motor illustrated in FIG. 8.
Figure 8:
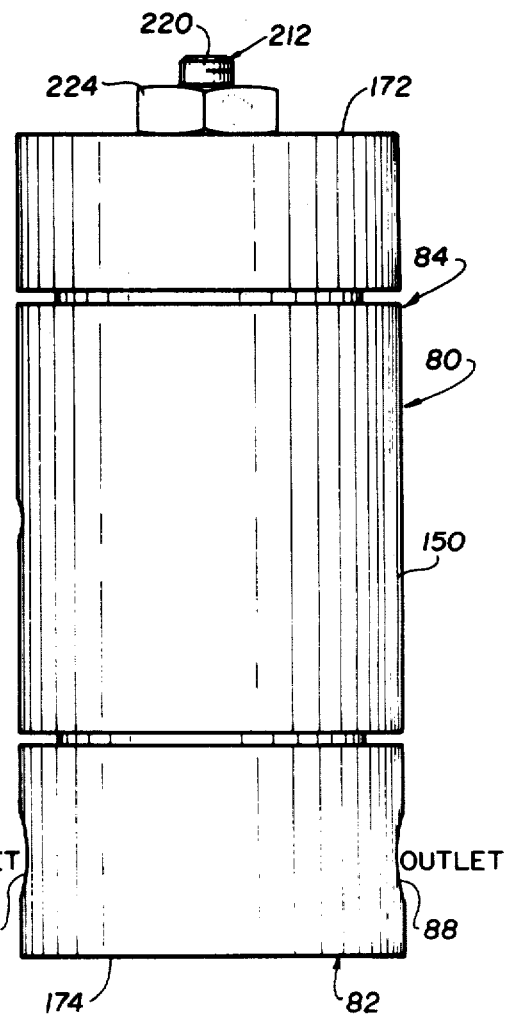
FIG. 8 is a front plan view of a fluid motor that may be utilized within the system illustrated in FIGS. 3 through 7.

FIG. 7 illustrates the operation of the system 10 when the user is desirous of turning off the power to the handpiece 12, which results in the tool 14 eventually ceasing to rotate. To deactivate the system 10 the finger 138 is brought into momentary engagement with actuation means 20. This touch and release, as illustrated by arrow 142 in FIG. 7, activates the switching means 65 such that the fluidic control means 70 and 72 perform a switching sequence resulting in the venting of the regulating means 84. As noted in FIG. 7, in comparison to FIG. 6, conduit 144 and 102 no longer contain the flow of pressurized fluid. Conduit 62 has the pressurized fluid contained therein now redirected into conduits 74 and 76.

Fourth valve means 99 is thus brought to its open position which through conduits 120 and 122 and the fluid is conduits 48 and 89 opens third valve means 98 which permits the escape of fluid from within regulating means 84 through conduit 116 and out through conduit 118. This bleeding results in the valve assembly closing within the regulating means 84. The "ON" signal previously present in conduit 102 to maintain first valve means 96 in its open position, as illustrated in FIG. 6, now ceases. This prevents any flow of drive fluid through conduit 92.

The closing of first valve means 96, as illustrated in FIG. 7, in turn closes coolant valve means 100 by eliminating the pressure of fluid in conduit 136. By closing of coolant valve means 100, the coolant fluid flow in coolant supply line 16 ceases. Therefore, the pressure in gauge 34 would return to the original indication as contained in the system 10 in the condition illustrated in FIG. 3.

Depending upon the parameters of the components of the system, it would be brought back to essentially the condition illustrated in FIG. 3 in approximately 0.5 to 2 seconds of time. At that point the system may be readily reactivated such that the user may select a different speed for performing dental drilling or other applications. In this manner changing speeds of the drill 14 is also obtained. For example, if the speed of RPM+2 has been reached by the user in the sequence of steps illustrated in FIGS. 3 through 6, and thereafter a lower speed of RPM+1 is desired, the system 10 is recycled to this lower speed. This is also true if one desires to go from a lower speed to a greater speed.

FLUID MOTOR

FIGS. 8 through 13 illustrate one of two preferred embodiments of a fluid motor 80. FIG. 14 illustrates the other of the two preferred embodiments of a fluid motor.

To further understand and appreciate the ability of the fluid motor 80 to vary the volume and pressure to the handpiece 12, reference is made to FIGS. 11, 12 and 13. The fluid motor 80 has two major components, namely the valve or transducer means 82 and regulating means 84. Sealed housing means 150 is provided and includes chamber means 152 associated therewith. The chamber means 152 is divided into a first or drive chamber 154 and a second or control chamber 156 in sealed relationship from each other.

The housing means 150 may include wall means 158 having an axially extending bore 160 therein, which may have a circular cross-section. The wall means 158 has an outer surface 162 and longitudinally spaced apart under and lower ends 164 and 166 respectively. Spaced apart end walls or closures 168 and 170 are provided.

The closures 168 and 170 may have outer or terminal ends 172 and 174 spaced from each other. End wall 168 may have an outer wall 176 and end wall 170 may have an outer wall 180. Outer walls 176 and 180 may be of a diameter equal to outer surface 162.

Wall means 158 is provided with a control opening 182 to provide compressed fluid to chamber 156. The chamber 156 is provided with first movable or resilient means 184 at one end thereof and second movable or resilient means 186 at the other end of chamber 156. In effect, the volume of chamber 156 is defined by the cross-sectional area of bore 160 and the longitudinal dimension between the inner surfaces 188 and 190 of the movable means 184 and 186, respectively. The movable means 184 and 186 may be in the form of a diaphragm or flexible member capable of being displaced to alter the volume of the control chamber 156.

Mounting means 200 is associated with the outer portions or ends 192 of the movable means 184 and 186. The movable means 184 has an outer surface 194, and the movable means 186 having an outer surface 196. The mounting means 200 is provided to retain the outer portions 192 in fixed mounted relationship such that the inner portion 202 of each of the movable means 184 and 186 may be displaced relative to its respective outer end or portion 192. Biasing means 205 is provided between the first and second resilient means 184 and 186. The biasing means 205 may be in the form of a compression spring and situated between retainment elements or washers 206.

To maintain proper alignment, each retainment element 206 may have an outer lip 208 to aid in retaining biasing means 205 seated therein. The biasing means 205 applies a first or biasing force against movable means 184 in the direction of arrow 210. The force of the biasing means 205 may be varied by pressure setting means 212.

The mounting means 200 may include a threaded neck portion 214 extending from one end of the closures 168 and 170. The neck portion 214 is received within a threaded counterbore 216 to sandwich the outer end 192 of each of the respective movable means 184 and 186. The pressure setting means 212 is operatively connected to the second movable means 186 for adjusting the force applied to the first movable means 184 by the biasing means 205.

The pressure setting means 212 may include a threaded element 220 having one end 222 for adjusting the position of the second movable means 186. A locking element 224 is threadably connected to the threaded element 220 for retaining the threaded element 220 in a selected position. A force applying member 225 and a retaining element 226 may be interposed between the end 222 and the outer surface 196 of movable element 186. The adjustment of the threaded element 220 will provide desired changes in the first or pre-loading force indicated by arrow 210.

This pre-loading force will generally deflect the second movable means 186 by a certain amount, which in turn applies a force to the first movable means 184. The first movable means 184 operates in conjunction with a valve assembly 230 that is interposed between inlet 86 and outlet 88. Adjustment of the valve assembly 230 to various positions in response to the pressure in chamber 156 will alter the flow of drive fluid to the handpiece 12.

The valve assembly 230 includes body part 232 having a passage 234 extending therethrough. The body part 232 may have an outer surface 235 mounted within a wall casing 236 contained on closure 170. A valve member 238 is located in the passage 234 with a valve seat 240 formed at one end of the body part 232. The valve member 238 moves axially in the passage 234 in response to displacement of the first movable means 184. The valve member 238 has a valve head 242 at one end thereof adapted for movement to and away from the valve seat 240 to vary the spacing therebetween so as to regulate the flow of drive fluid through the passage 234 between the inlet 86 and the outlet 88. A valve base 244 is provided at the other end of valve member 238 for engagement with the outer surface 194 of the first movable means 184. A sealing element or washer 245 may be provided on the upper surface 246 of the valve head 242 to be brought into sealing engagement with the valve seat 240.

The valve member 238 does not have to be mechanically coupled or linked to the upper surface 246 of the valve head 242. To bias the valve base 244 against the first movable means 184, there is provided spring means 248 which includes a spring 250 to apply the force in the direction of arrow 252. The spring 250 may be mounted in telescopic relationship to an outer surface 254 of the valve head 242 and abut against a lip or ridge 256. The other end of spring 250 is mounted in a seat or pocket 258.

The sequence of operation of fluid motor 80 is illustrated in FIGS. 11, 12 and 13. A first or initial force is applied in the direction of arrow 210 by the biasing means 205. This, in effect, provides a pre-loading condition on the regulating means 84. In this condition, as illustrated in FIG. 11, there would be sufficient deflection in the first movable means 184 to provide a spacing between washer 245 and valve seat 240. This opening in passage 234 permits a flow of drive fluid through the pressure transducer means 82 immediately upon the opening of the downstream first valve means 96. For example, if the primary pressure from source 42 is 35 PSI, the secondary pressure may be 20 PSI and the flow occurring in the direction of arrows 260. At the same time there would be a pressure buildup in the pressure chamber 154. The position of the fluid motor illustrated in FIG. 11 would coincide with the system as illustrated in FIG. 4, which would be that the tool 14 was rotating at RPM min.

FIG. 13 coincides with the condition illustrated in FIG. 5 when the second valve means 97 is open and fluid continues to enter, and build up pressure within control chamber 156. This pressure buildup is illustrated by force applying arrow 262. As explained before, at such time as the desired speed of rotation of tool 14 is obtained, the second valve means 97 is closed, as illustrated in FIG. 6. The pressure chamber 156 would at that moment be providing a secondary force indicated by arrow 264, that is directed against the first movable means 184. This secondary force is sufficient to move the valve head 242 rearwardly so as to increase the spacing defined between the valve seat 240 and washer 245.

Therefore, the pressure buildup in the pressure chamber 156 acts to overcome the oppositely directed force of spring 250 such that the first movable means 184 is deflected an amount that is in a ratio relative to the pressure buildup in the pressure chamber 156. The position illustrated in FIG. 13 will be maintained for the period of time that the sealed chamber is prevented from venting. As previously discussed with respect to FIG. 7, when the third valve means 98 is vented, the pressure chamber 156 will return to its original equilibrium, as illustrated in FIG. 12.

FIG. 12 illustrates the valve assembly 230 being in a completely closed condition. This occurs upon the closing of the first valve means 96 which results in a pressure buildup in the drive chamber 154. This pressure buildup is sufficient to overcome the first force indicated by arrow 210 against the first movable means 184. The result is that the sealing element 245 is brought into abutting engagement with the valve seat 240. Sequencing of the system 10 will permit a recycling of the fluid motor means 80 through the conditions illustrated and described above. Obviously, the pressure setting means 212 may be regulated to control the first force illustrated by arrow 210.

Referring now to FIG. 14, there is illustrated a second embodiment of a fluid mptor 80a which is designed to provide the same end results as the embodiment illustrated in FIGS. 8 through 13. The exterior configuration of both embodiments may be identical to each other. In the embodiment of FIG. 14 the first movable means 184a and second movable means 186a may be piston-like elements having a peripheral or annular sealing gasket 266a in surrounding relationship thereto to provide a seal against the bore wall 160a of the pressure chamber 156a. The biasing means 205a may be mounted in a seat 268a provided in each of the inner surfaces of first movable means 184a and second movable means 186a.

The pressure setting means 212a operates in the manner described above and the front end 222a of threaded member 220a is coupled to the second movable means 186a. The first movable means 184a may be formed of two sections 270a designed to abut each other and having sealing elements 266a mounted thereon. Annular sealing elements 272a are provided between the wall means 158a and the closures 168a and 170a.

Accordingly, the first and second movable means 184a and 186a are each free to move independently of each other within the axial bore 160a. The forces applied will be dependent upon the adjustments made by the pressure setting means 212a. In this manner the fluid motor means 80a may be utilized within the system described herein.

ADDITIONAL CONTROL SYSTEM EMBODIMENT

Figure 15:
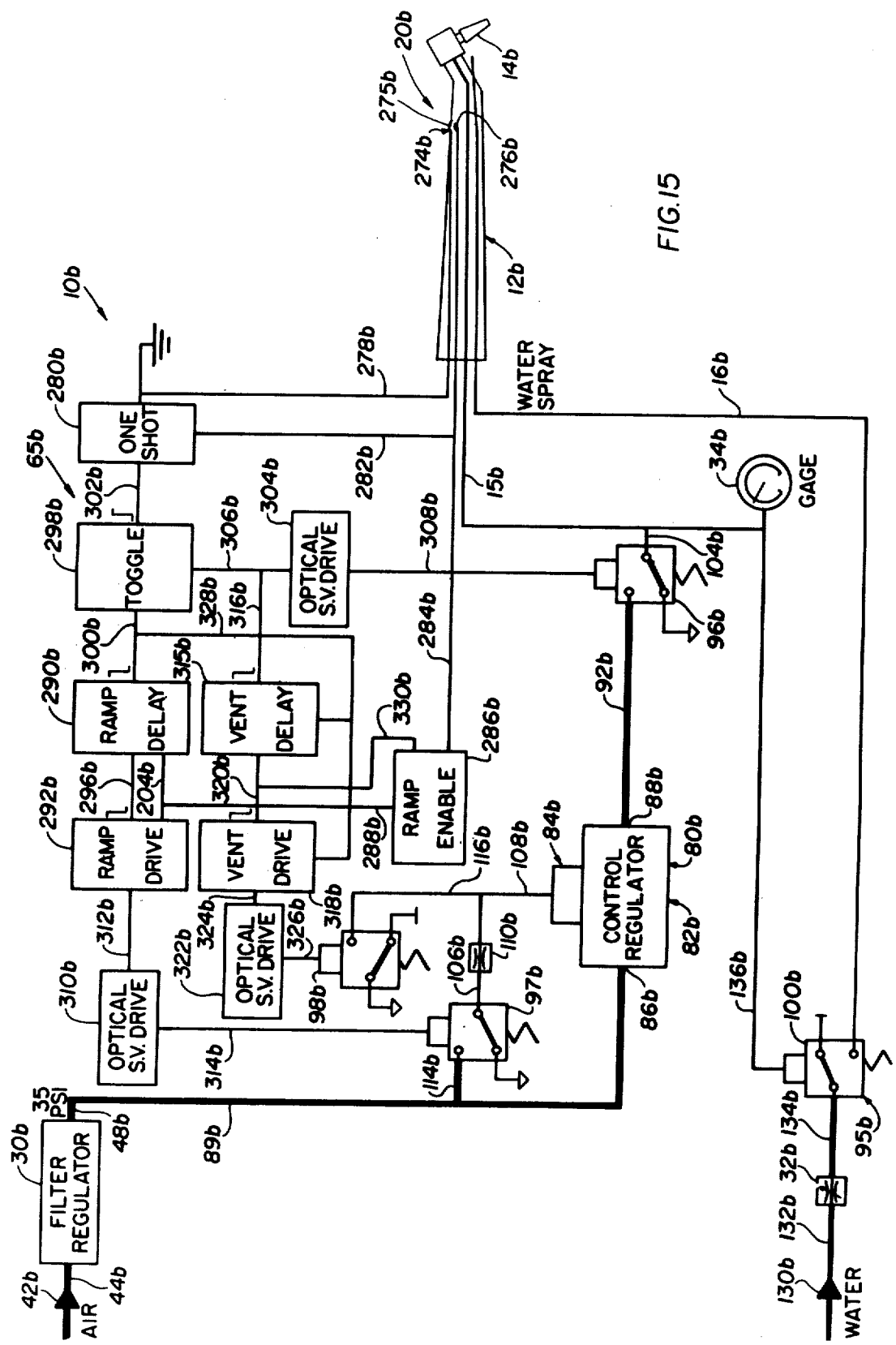
FIG. 15 is a schematic representation of a flow diagram illustrating another embodiment of the present invention similar to that illustrated in FIGS. 3-7, with electronic means controlling the selection of the desired power to the handpiece.
Figure 16:
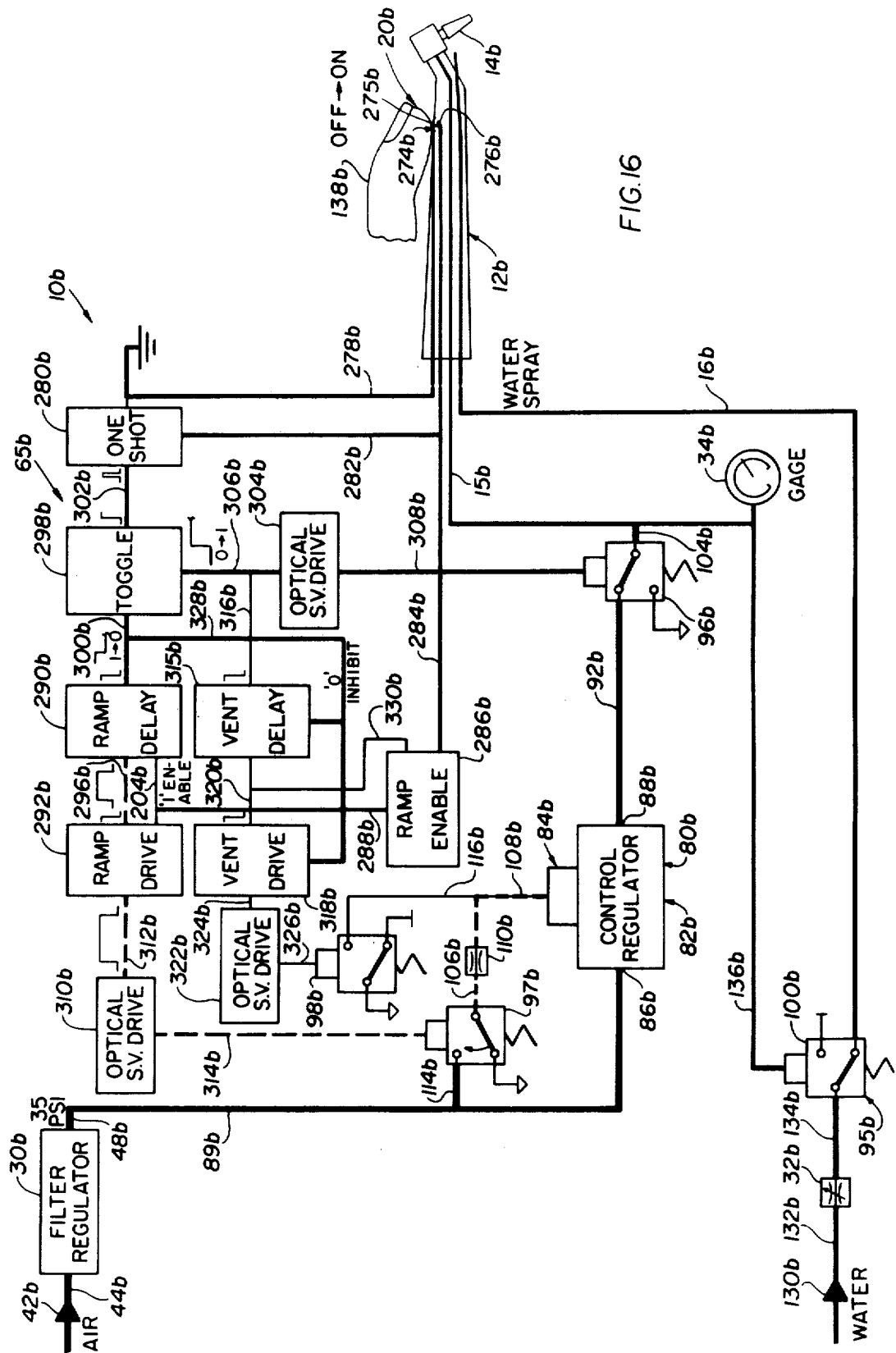
FIG. 16 is a view similar to FIG. 15 illustrating the system of FIG. 15 in a second operating position.

Referring to FIGS. 15–17, there is illustrated another embodiment of a control system 10b that may be utilized to regulated the speed of a dental tool 14b associated with a dental handpiece 12b. The system 10b illustrated in FIGS. 15, 16 and 17 performs the same end result as that previously illustrated and described with respect to FIGS. 3 through 7. The actuation means 20b and switching means 65b are electronically controlled by an automatic electrical control system shown as a functional block diagram, in a manner to obtain changes of pressure within the fluid motor means 80b in the same manner as previously described.

A source of fluid indicated at 42b is available through conduit 44b and fluid control means 30b which is coupled by conduits 48b and 89b to the pressure transducer means 82b. In addition, conduit 114b provides through second valve means 97b the means for pressurizing the regulating means 84b. Conduits 106b and 108b couple the second valve means 97b to the regulating means 84b, with restrictor 110b positioned therebetween.

Third valve 98b is utilized for venting the regulating means 84b through conduit 116b as required. First valve means 96b operates to permit flow from conduit 92b through drive fluid supply line 15b. Coolant valve means 100b acts to provide the desired flow of coolant from source 130b. The actuating means 20b in this embodiment incorporates a finger switch 274b having a pair of contacts 275b and 276b contained within the handpiece 12b such that depression by the finger of the user provides the input signal to the power means 65b which is designed to operate in an equivalent manner to the fluidic switching means previously discussed.

FIG. 15 illustrates the system 10b in a condition which is equivalent to that illustrated in FIG. 3. The finger switch 274b activates the system 10b to perform essentially the following functions, on and off of the system 10b, speed control of the tool 14b and a vent function which vents the fluid motor 80b so as to terminate the flow of drive fluid through drive fluid line 15b. Momentary toggling of finger switch 274b activates the electronic switching means 65b that will permits minimum flow of drive fluid through pressure transducer means 82b.

By depressing and holding the finger switch 274b for an arbitrary but fixed period of time, the speed of rotation of tool 14b is increased by the increase in flow through the pressure transducer means 82b, as illustrated with respect to FIG. 16. Subsequent engagement of the finger switch 274b activates system 10b, as illustrated in FIG. 17, to vent the regulating means 84b through third valve means 98b such that the pressure in the regulating means 84b is reduced to its initial value. The sequence of operation may then be repeated as required.

Finger switch 274b has lead 278b extending between contact 275b tc signal ground. Lead 282b extends between contact 276b and one shot multivibrator 280b. Contact 276b is also connected via lead 284b to ramp enable 286b. Depressing and releasing finger switchs 274b triggers one shot multivibrator 1280b and enable ramp 286b. The enable ramp 286b is connected via lead 288b to ramp delay 290b. Ramp delay 290b is connected to ramp drive 292b via lead 204b which is also connected to lead 288b.

Accordingly, the controlling means formed by the switching means 65b, valve means 96b and the fluid motor means 80b is activated by depressing of finger switch 274b, which allows ramp delay 209b and ramp drive 292b to process input signals. Toggle 298b is connected via lead 300b to ramp delay 290b, and via lead 302b to one shot multivibrator 280b. Toggle 298b changes states during the positive transition of the output from the one shot multivibrator 280b. Toggle 298b has two outputs that are complementary. A positive going output pulse signals the optical solenoid drive 304b, via lead 306b, to energize the solenoid of first valve means 96b via lead 308b. First valve means 96b in its open position, as illustrated in FIG. 16, supplies drive fluid to the turbine drive of handpiece 12b.

The vent delay circuit is inactive because it requires a negative going input. The negative going pulse output of the toggle 298b also activates the ramp delay 290b via lead 300b, however, since the finger switch 274b is only momentarily closed, the ramp delay 290b is then reset. This permits flow of drive fluid from fluid conduit 48b associated with fluid drive regulator 30b, through conduit 89b and in turn 92b at the minimal flow rate through the pressure transducer means 82b.

To obtain speed control, the closure time of the finger switch 274b must exceed the delay time of the ramp delay 290b. The ramp drive 292b then initiates a drive signal to the optical solenoid drive 310b via lead 312b. Optical solenoid drive 310b actuates the solenoid associated with second valve means 97b via lead 314b. This signal causes second valve means 97b to be brought into an open position. In the open position of second valve means 97b, the fluid pressure flowing through the fluid motor means 80b is increased.

As long as the finger switch 274b remains depressed, the turbine speed will increase at a constant rate until a maximum speed is obtained. The flow from second valve means 97b through conduits 106b and 108b is illustrated by dashed lines in FIG. 16. In similar fashion the signal via leads 296b, 312b and 314b are illustrated by dashed lines in FIG. 16, to illustrate that this signal remains as long as the finger switch 274b remains depressed. The speed of the system 10b is maintained at the highest commanded rate when the finger is removed from the finger switch 274b. As long as the finger 138b depresses finger switch 274b, any desired speed can be commanded and maintained by releasing the initial ramp command at the desired rate.

If for any reason a lower speed is again required, or the unit is to be in effect turned off, then the finger switch 274b is once again depressed for an off command signal. After a pause, the duration of which is adjustable, the finger switch 274b is once again depressed until the desired speed is obtained and thereafter is released.

Whenever the system 10b is commanded to go from an on to an off state, a negative going pulse from toggle 298b initiates the vent delay 315b, via lead 316b. After an adjustable period the vent drive 318b is activated via lead 320b. This provides a drive signal for the optical solenoid drive 322b which is connected thereto via lead 324b. The optical solenoid drive 322b in turn energizes, via lead 326b, the solenoid of third valve means 98b. When third valve means 98b is activated the regulating means 84b is returned to its initial preset position, and is simultaneously vented. As illustrated in FIG. 17, third valve means 98b is in its open position and control fluid may flow through conduit 116b.

Actuation of first valve means 96b via lead 308b energizes coolant valve means 100b to permit coolant fluid to flow through feed line 16b. Toggle 298b is connected by lead 328b to vent delay 315b and vent drive 318b so that a positive going pulse (0 to 1) from the toggle 298b will enable them, this also permits a negative going signal (1 to 0) to be processed by the vent drive 318b and vent delay 315b.

Lead 330b connects ramp enable 286b to lead 320b to provide a signal to the ramp enable 286b causing it to provide a "0" or inhibit signal to the ramp drive 292b and ramp delay 290b via lead 288b, thereby preventing optical drive 310b from being activated during the venting portion of the cycle.

The switching means 65b is powered from a conventional source of 110 volts AC, not shown, and includes conventional solid state modules to perform the required functions.

It is to be noted that the toggle circuit arrangement 298b is activated on a positive going pulse. The ramp drive circuit arrangement 292b, ramp delay circuit arrangement 290b vent drive curcuit arrangement 318b and vent delay circuit arrangement 315b are all activated on a negative going pulse. The positive and negative going pulses are defined as negative when going from a high logic state of 1 to a low logic state of 0 and positive when at a low logic state of 0 changing to a high logic state of 1.

As described hereinbefore the present invention will be explained with reference to FIGS. 15, 16 and 17. Although these figures relate to a dental appartus it is to be understood that other types of mechanisms which utilize fluid motors may be utilized equally as well.

The closing of switch 274b completes the ground return circuit from line 278b to 282b, thereby causing the one shot multivibrator 280b to provide an output pulse on line 302b. Simultaneously therewith the ground is placed on lead line 284b, thereby activating the ramp enable circuit 286b. The ramp enable circuit arrangement 286b provides an output on line 288b which enables the ramp drive 292b and ramp delay 290b circuit arrangements. The positive going pulse being applied to the toggle circuit arrangement 298b causing it to provide a complimentary output signal voltage on leads 300b and 306b.

The pulse appearing on line 300b as shown in FIG. 16 will go from a high level of 1 to 0. The pulse appearing on line 306b will go from a 0 a 1. Since ramp delay circuit arrangement 290b will be activated by a negative going signal, it will provide an output pulse which is coupled to the ramp drive circuit arrangement 292b. The output appearing on lead 312b is coupled to the optical drive 310b which provides an energizing output on line 314b activating control valve 97b, control valve 97b being moved to an open condition allows additional fluid to flow into control regulator 82b, thereby increasing the fluid flow in the line 92b which is coupled to valve 96b.

The 0 signal appearing on line 200b is coupled on line 328b to the vent drive circuit arrangement 318b and the vent delay circuit arrangement 315b which are inhibited because of the 0 state, thus providing no output.

The optical drive 304b having received a positive going pulse provides an output on line 308b which energizes control valve 96b thus allowing the fluid flow to continue on line 15b where it drives the fluid motor output to 14b. In the preferred embodiment this is known as the minimum operational speed.

With the switch 274b closed for an increasing period of time the output from the ramp drive circuit arrangement 292b will continue providing an output thereby causing the fluid flow to increase directly in relationship to the length of time switch 274b is maintained in an activated or closed position. This is course will cause the speed of the tool 14b of the handpiece 12b to increase correspondingly therewith.

Release of switch 274b and momentarily pressing it again causes the output of the toggle circuit arrangement 298b to change states thus providing an output on line 300b going from a 0 state to a plus 1 state, the complimentary output voltage appearing on line 306b changes from a 1 state to a 0 state. Since ramp delay circuit is activated only on a negative going pulse it no longer can accept the incoming signal on line 300b. The 1 signal level appearing on line 328b enables the vent delay circuit arrangement 315b, and the vent drive circuit arrangement 318b. The output of vent delay circuit 315b causes the ramp enable circuit arrangement 286b to provide on line 288b a 0 output which inhibits both the ramp drive 292b and the ramp delay 290b circuit arrangements.

The output of vent drive circuit arrangement 318b is applied to optical drive 322b which therefore provides an output signal on line 326b energizing valve 98b, valve 98b being activated completes a path along lead 116b which allows for the venting of the control regulator 82b, thereby reducing pressure to P min. The voltage from toggle 298b on line 306b changes to a 0 state inhibiting optical drive 304b which deenergizes control valve 96b stopping the fluid flow on line 15b, thereby stopping tool 14b. Thus it has been shown that an electrical circuit arrangement may be used to perform the same functions as the fluidic control circuitry described hereinbefore.

Although illustrative embodiments of the invention have been described in detail herein with reference to the accompanying drawings, it is to be understood that the invention is not limited to the precise embodiments and that various changes and modifications may be effected therein without departing from the scope or spirit of the invention.

What is claimed is:

1. A system for controlling the flow of a drive fluid from a source along a path comprising:
   A. fluid motor means operatively connected to said drive fluid path for providing variable output speed to a tool in response to the flow and pressure of said drive fluid along said path,
   B. control valve means disposed in said drive fluid flow path between said source of drive fluid and said fluid motor means for controlling the flow and pressure of said drive fluid,
   C. switching means coupled to said control valve means for controlling said control valve means, and
   D. activating means coupled to said switching means for controlling said control valve means proportionally to the length of time of activating said activating means and maintaining the resulting tool output speed after de-activating said activating means.

2. A system as defined in claim 1, wherein said activation means comprises a pair of switch contacts.

3. A system as defined in claim 1, wherein said switching means comprises:
   a. first means for providing one of complimentary output signal voltages upon receiving an input signal from said activating means,
   b. second means coupled to said first means for providing an output upon receiving said one of said complimentary signal voltages in excess of a predetermined minimum of time, said second means output signal voltage continuing for a length of time relating to said activating means activating time, said second means output being coupled to said control valve means for controlling the flow and pressure of said drive fluid,
   c. third means coupled to said second means for providing an enabling signal voltage to said second means continuing for a length of time relating to said activating means activating time,
   d. vent means coupled to said control valve means for venting said fluid pressure of said control valve means to a predetermined level, and
   e. fourth means coupled to said vent means for the activation thereof by a signal upon receiving the other of said complimentary output signal voltages, said fourth means also being coupled to said third means for causing said third means to remove said enable voltage when providing said activation signal.

4. A system as defined in claim 3, wherein said first means includes a one shot multivibrator coupled to a toggle circuit arrangement for providing said complimentary voltages when said one shot multivibrator is activated by said activating means.

5. A system as defined in claim 3, wherein said second means includes a ramp delay circuit arrangement coupled to a ramp drive circuit arrangement for activating a second control valve means, said second control valve means providing additional fluid to said first named control valve means upon activation thereof.

6. A system as defined in claim 3, wherein said third means includes a ramp enable circuit arrangement responsive to the activation of said activation means.

7. A system as defined in claim 3, wherein said fourth means includes a vent delay circuit arrangement coupled to a vent drive circuit arrangement for activation of a third control valve means for venting said first named control valve means.

8. A system as defined in claim 1, wherein said first named control valve means includes a control regulator for varying the amount of drive fluid flow and a serially connected first control valve for directing said drive fluid to said fluid motor means when activated.

9. A system as defined in claim 1, further including a second control valve coupled to said first control valve and activated simultaneously therewith for providing a flow of coolant adjacent the tool.

10. A system as defined in claim 1, wherein said activating means is on a handpiece for manual activation by the user thereof.

11. A system as defined in claim 1, wherein said switching means is automatically cycled for controlling said control valve means to stop said flow of drive fluid upon subsequent activation of said activating means.

* * * * *